United States Patent
Shimada et al.

(10) Patent No.: US 10,920,349 B2
(45) Date of Patent: Feb. 16, 2021

(54) MULTILAYER NONWOVEN FABRIC, STRETCHABLE MULTILAYER NONWOVEN FABRIC, FIBER PRODUCT, ABSORBENT ARTICLE, AND SANITARY MASK

(71) Applicant: MITSUI CHEMICALS, INC., Tokyo (JP)

(72) Inventors: Koichi Shimada, Chiba (JP); Kenichi Suzuki, Ichihara (JP); Shouichi Takaku, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 246 days.

(21) Appl. No.: 15/556,543

(22) PCT Filed: Mar. 9, 2016

(86) PCT No.: PCT/JP2016/057461
§ 371 (c)(1),
(2) Date: Sep. 7, 2017

(87) PCT Pub. No.: WO2016/143833
PCT Pub. Date: Sep. 15, 2016

(65) Prior Publication Data
US 2018/0051405 A1    Feb. 22, 2018

(30) Foreign Application Priority Data
Mar. 9, 2015   (JP) ................. 2015-046378

(51) Int. Cl.
*D04H 3/16*     (2006.01)
*B32B 5/26*     (2006.01)
(Continued)

(52) U.S. Cl.
CPC ............ *D04H 3/16* (2013.01); *A41D 13/11* (2013.01); *A61F 13/15* (2013.01); *A62B 18/02* (2013.01);
(Continued)

(58) Field of Classification Search
CPC .......... D04H 3/16; D04H 1/4291; B32B 5/04; B32B 5/26; B32B 2262/14
(Continued)

(56) References Cited

U.S. PATENT DOCUMENTS 5,366,792 A * 11/1994 Shirayanagi ............. B32B 5/26
                                                        428/196
5,470,639 A    11/1995 Gessner et al.
(Continued)

FOREIGN PATENT DOCUMENTS

CN    101432478 A    5/2009
CN    103221600 A    7/2013
(Continued)

OTHER PUBLICATIONS

International Search Report (PCT/ISA/210) dated May 24, 2016, by the Japanese Patent Office as the International Searching Authority for International Application No. PCT/JP2016/057461.
(Continued)

*Primary Examiner* — Peter Y Choi
(74) *Attorney, Agent, or Firm* — Buchanan, Ingersoll & Rooney PC

(57) ABSTRACT

A multilayer nonwoven fabric includes: an elastic nonwoven fabric containing a specific low crystalline polypropylene; and a mixed fiber spunbonded nonwoven fabric disposed on at least one surface of the elastic nonwoven fabric, wherein the mixed fiber spunbonded nonwoven fabric contains a long fiber of a thermoplastic elastomer (A) and a long fiber of a thermoplastic elastomer (B) other than the thermoplastic
(Continued)

elastomer (A), in a ratio of 10 to 90% by mass:90 to 10% by mass ((A):(B), with the proviso that (A)+(B)=100% by mass).

13 Claims, 1 Drawing Sheet

(51) Int. Cl.
| | | |
|---|---|---|
| *D04H 3/007* | (2012.01) | |
| *A41D 13/11* | (2006.01) | |
| *A61F 13/15* | (2006.01) | |
| *A62B 18/02* | (2006.01) | |
| *B32B 5/02* | (2006.01) | |
| *B32B 5/04* | (2006.01) | |
| *D01F 6/06* | (2006.01) | |
| *D04H 1/4291* | (2012.01) | |
| *D04H 3/153* | (2012.01) | |

(52) U.S. Cl.
CPC ............... *B32B 5/022* (2013.01); *B32B 5/04* (2013.01); *B32B 5/26* (2013.01); *D01F 6/06* (2013.01); *D04H 1/4291* (2013.01); *D04H 3/007* (2013.01); *D04H 3/153* (2013.01); *B32B 2262/0253* (2013.01); *B32B 2262/12* (2013.01); *B32B 2262/14* (2013.01); *B32B 2555/02* (2013.01)

(58) Field of Classification Search
USPC ......................................................... 442/381
See application file for complete search history.

(56) References Cited

U.S. PATENT DOCUMENTS

| | | |
|---|---|---|
| 2004/0067710 A1 | 4/2004 | Tsujiyama et al. |
| 2005/0130544 A1 | 6/2005 | Cheng et al. |
| 2008/0014819 A1 | 1/2008 | Suzuki et al. |
| 2008/0199673 A1 | 8/2008 | Allgeuer et al. |
| 2010/0093244 A1* | 4/2010 | Motomura .............. B32B 5/022 442/329 |
| 2010/0255255 A1 | 10/2010 | Kawakami et al. |
| 2012/0164908 A1* | 6/2012 | Kunimoto ......... A61F 13/51104 442/401 |
| 2013/0070518 A1 | 3/2013 | Eigler et al. |
| 2013/0239283 A1 | 9/2013 | Yokoyama et al. |

FOREIGN PATENT DOCUMENTS

| | | |
|---|---|---|
| EP | 2 022 879 A1 | 2/2009 |
| JP | S64-20322 A | 1/1989 |
| JP | H-07-503502 A | 4/1995 |
| JP | 2001-140158 A | 5/2001 |
| JP | 2001-303421 A | 10/2001 |
| JP | 2003-013349 A | 1/2003 |
| JP | 2004-238775 A | 8/2004 |
| JP | 2005-089870 A | 4/2005 |
| JP | 2007-321292 A | 12/2007 |
| JP | 2008-213284 A | 9/2008 |
| JP | 2009-504933 A | 2/2009 |
| JP | 2009-062667 A | 3/2009 |
| JP | 2009-079341 A | 4/2009 |
| JP | 2012-012759 A | 1/2012 |
| KR | 10-2008-0022207 A | 3/2008 |
| KR | 10-2013-0081705 A | 7/2013 |
| WO | 2005/121192 A1 | 12/2005 |
| WO | WO 2007/138733 A1 | 12/2007 |
| WO | WO 2009/063892 A1 | 5/2009 |
| WO | 2011/016343 A1 | 2/2011 |
| WO | WO 2012/070518 A1 | 5/2012 |

OTHER PUBLICATIONS

Written Opinion (PCT/ISA/237) dated May 24, 2016, by the Japanese Patent Office as the International Searching Authority for International Application No. PCT/JP2016/057461.
International Search Report (PCT/ISA/210) dated May 24, 2016, by the Japanese Patent Office as the International Searching Authority for International Application No. PCT/JP2016/057462.
Written Opinion (PCT/ISA/237) dated May 24, 2016, by the Japanese Patent Office as the International Searching Authority for International Application No. PCT/JP2016/057462.
Decision of Refusal issued by the Japanese Patent Office in corresponding Japanese Patent Application No. 2017-505384 dated Oct. 16, 2018 (6 pages including partial English translation).
Office Action issued by the Korean Patent Office in corresponding Korean Patent Application No. 2017-7025133 dated Jul. 19, 2018 (8 pages including partial English translation).
Notice of Opinion of Examination issued by the Taiwanese Patent Office in corresponding Taiwanese Patent Application No. 10820619540 dated Jul. 1, 2019 (16 pages including partial English translation).
Office Action dated May 15, 2020, by the Intellectual Property India in corresponding Indian Patent Application No. 201717031844 with an English Translation of the Office Action. (5 pages).

* cited by examiner

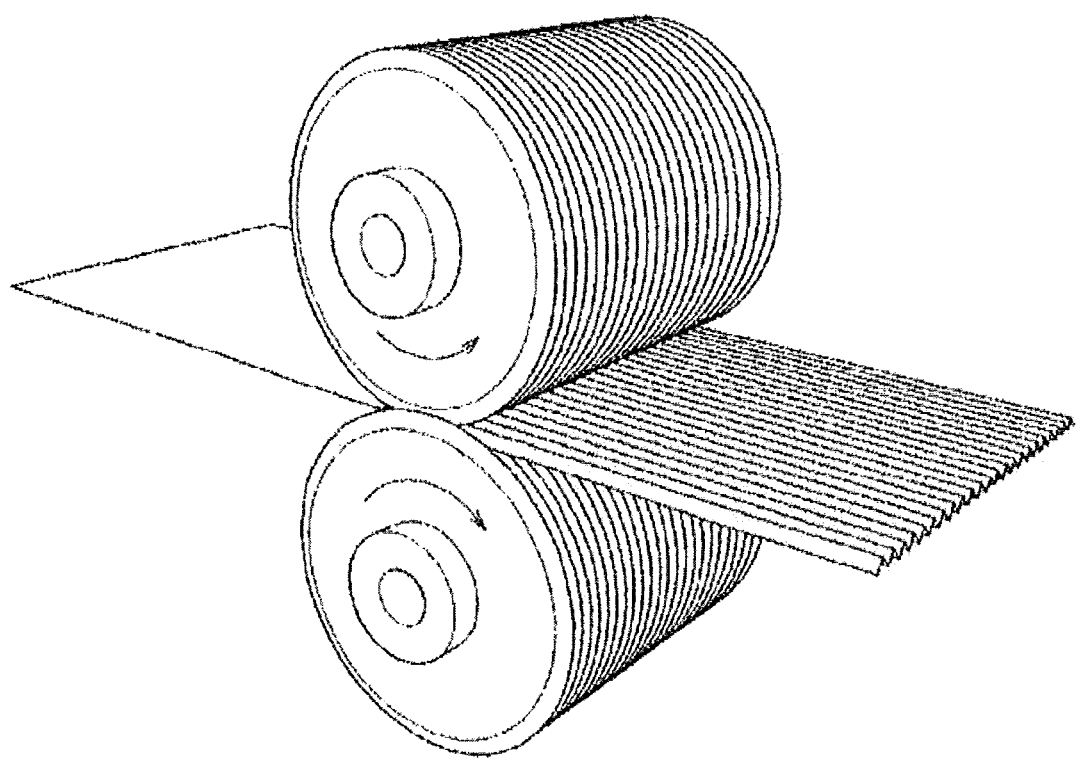

MULTILAYER NONWOVEN FABRIC, STRETCHABLE MULTILAYER NONWOVEN FABRIC, FIBER PRODUCT, ABSORBENT ARTICLE, AND SANITARY MASK

TECHNICAL FIELD

The present invention relates to a multilayer nonwoven fabric, a stretchable multilayer nonwoven fabric, a fiber product, an absorbent article, and a sanitary mask.

BACKGROUND ART

In recent years, nonwoven fabrics are widely used in various applications because of their excellent air breathability and flexibility. For that reason, the nonwoven fabrics require various characteristics in accordance with their applications, and improvements in their characteristics.

For example, excellent waterproofness and moisture permeability are required for nonwoven fabrics which are used for hygiene materials such as disposable diapers and sanitary napkins, and for backings for poultices, and the like. In addition, stretchability and bulkiness are also required depending on the sections to which the fabrics are used.

As a method of imparting stretchability to a nonwoven fabric, a method of using a thermoplastic elastomer as a raw material of a spunbonded nonwoven fabric (see, for example, Japanese National-Phase Publication (JP-A) No. H07-503502), and a method of using a low crystalline polypropylene (see, for example, Japanese Patent Application Laid-Open (JP-A) Nos. 2009-62667 and 2009-79341), and the like have been proposed.

Patent Literature 2 or 3 proposes that a highly crystalline polypropylene or a release agent is added to a low crystalline polypropylene in order to improve stickiness and the like of a spunbonded nonwoven fabric. International Publication No. 2012/070518 discloses a multilayer of a nonwoven fabric containing a low crystalline polypropylene and an extensible spunbonded nonwoven fabric.

SUMMARY OF INVENTION

Technical Problem

According to the method described in JP-A No. 2009-62667 or JP-A No. 2009-79341, in order to prevent a spunbonded nonwoven fabrics containing a low crystalline polypropylene from adhering to various rotary units in apparatuses during steps such as embossing or to any other regions which are brought into contact with the nonwoven fabrics during production of the spunbonded nonwoven fabric using the low crystalline polypropylene, it is necessary to increase the amount of the highly crystalline polypropylene or release agent to be added to the low crystalline polypropylene. As a result, the resulting spunbonded nonwoven fabric tends to have a greater residual strain and to be inferior in stretchability. According to the method described in International Publication No. 2012/070518, stretchability is maintained by stacking a low crystalline polypropylene and an extensible spunbonded nonwoven fabric, but a further improvement in stretchability is strongly demanded.

In applications such as hygiene materials (such as disposable diapers and sanitary napkins), and backings for poultices, stress at extending is required to be small so that the materials can be mounted with a weak force, and stress at recovering is required to be large so as to prevent gap while being mounted. That is, in the above applications, it is required not only to decrease the value of stretch characteristics (ratio of stress at extending/stress at recovering) but also to decrease the absolute value of the stress at extending and to increase the absolute value of the stress at recovering.

In producing processes of hygiene materials such as disposable diapers and sanitary napkins, nonwoven fabrics are heat sealed and bonded together in some cases. A problem that sealing strength is lowered occurs in a case in which a sealing time in the heat sealing process is shortened for the purpose of speeding up the production. An increase in a sealing temperature causes a problem that a sealed portion becomes hard. For this reason, nonwoven fabrics capable of being heat-sealed at as low a temperature as possible are strongly required while a soft texture is maintained.

In view of the above-described problems, it is an object of the present invention to provide a multilayer nonwoven fabric excellent in moldability during production, less sticky, excellent in stretchability and low-temperature heat sealability, and a stretchable multilayer nonwoven fabric, a fiber product, an absorbent article, and a sanitary mask which include the same.

Solution to Problem

Means for solving the above-mentioned problems includes the following embodiments.

<1> A multilayer nonwoven fabric, including:
an elastic nonwoven fabric containing a low crystalline polypropylene satisfying the following (a) to (f); and
a mixed fiber spunbonded nonwoven fabric disposed on at least one surface of the elastic nonwoven fabric,
wherein the mixed fiber spunbonded nonwoven fabric contains a long fiber of a thermoplastic elastomer (A) and a long fiber of a thermoplastic elastomer (B) other than the thermoplastic elastomer (A) in a ratio of 10 to 90% by mass:90 to 10% by mass ((A):(B), with the proviso that (A)+(B)=100% by mass):
(a) [mmmm]=20 to 60 mol %;
(b) [rrrr]/(1−[mmmm])≤0.1;
(c) [rmrm]>2.5 mol %;
(d) [mm]×[rr]/[(mr)]$^2$≤2.0;
(e) weight-average molecular weight (Mw)=10,000 to 200,000; and
(f) molecular weight distribution (Mw/Mn)<4,
wherein:
[mmmm] is a mesopentad fraction;
[rrrr] is a racemic pentad fraction;
[rmrm] is a racemic meso racemic mesopentad fraction; and
[mm], [rr] and [mr] are triad fractions.

<2> The multilayer nonwoven fabric according to <1>, wherein a maximum point elongation of the long fiber of the thermoplastic resin (B), in a case of being formed into the spunbonded nonwoven fabric, is 50% or more.

<3> The multilayer nonwoven fabric according to <1> or <2>, wherein the thermoplastic elastomer (A) is a thermoplastic polyurethane elastomer.

<4> The multilayer nonwoven fabric according to <3>, wherein:
the thermoplastic polyurethane elastomer has a solidification starting temperature of 65° C. or higher as measured by a differential scanning calorimeter (DSC); and
a number of particles of the thermoplastic polyurethane elastomer insoluble in a dimethylacetamide solvent measured by a particle size distribution measuring apparatus equipped with an aperture of 100 μm based on a pore electrical resistance method, is 3,000,000/g or less.

<5> The multilayer nonwoven fabric according to <3> or <4>,
wherein the thermoplastic polyurethane elastomer is a thermoplastic polyurethane elastomer satisfying the following relational expression (I):

$$a/(a+b) \leq 0.8 \qquad (I)$$

wherein:
a represents a total amount of fusion heat calculated from an endothermic peak in a range of 90° C. to 140° C., as measured by DSC; and
b represents a total amount of fusion heat calculated from an endothermic peak in a range from higher than 140° C. to 220° C. or lower, as measured by DSC.

<6> The multilayer nonwoven fabric according to any one of <1> to <5>, wherein the thermoplastic resin (B) is a polyolefin.

<7> The multilayer nonwoven fabric according to any one of <1> to <6>, wherein the thermoplastic resin (B) is a propylene polymer.

<8> The multilayer nonwoven fabric according to any one of <1> to <7>, wherein the thermoplastic resin (B) includes 99 to 80% by mass of a propylene polymer and 1 to 20% by mass of a high-density polyethylene.

<9> A stretchable multilayer nonwoven fabric obtained by drawing the multilayer nonwoven fabric according to any one of <1> to <8>.

<10> A fiber product including the multilayer nonwoven fabric according to any one of <1> to <8> or the stretchable multilayer nonwoven fabric according to <9>.

<11> An absorbent article including the multilayer nonwoven fabric according to any one of <1> to <8> or the stretchable multilayer nonwoven fabric according to <9>.

<12> A sanitary mask including the multilayer nonwoven fabric according to any one of <1> to <8> or the stretchable multilayer nonwoven fabric according to <9>.

Advantageous Effects of Invention

The present invention can provide a multilayer nonwoven fabric excellent in moldability during production, less sticky, excellent in stretchability and low-temperature heat sealability, and a stretchable multilayer nonwoven fabric, a fiber product, an absorbent article, and a sanitary mask which include the same.

BRIEF DESCRIPTION OF DRAWINGS

FIG. 1 is a schematic diagram of a gear drawing device.

DESCRIPTION OF EMBODIMENTS

Hereinafter, embodiments for carrying out the present invention will be described in detail. However, the invention is not limited to the following embodiments. In the following embodiments, constituent elements (including element steps and the like) are not indispensable unless otherwise expressly provided or except the case in which the constituent elements are apparently indispensable in principle. The same applies to numerical values and ranges of the constituent elements, and the invention is not limited thereby.

In the present specification, the term "step" includes not only a separate step but also a step that cannot be clearly distinguished from other steps as long as the object of the step is achieved. In the present specification, the notation "to" expressing a numerical range indicates a range including the numerical values before and after "to", as the minimum value and the maximum value, respectively. In the present specification, in a case in which plural kinds of substances corresponding to components exist in the composition, the content of each of the components in the composition refers to the total amount of the plural substances in the composition unless otherwise specified.

<Multilayer Nonwoven Fabric>

A multilayer nonwoven fabric of the invention includes: an elastic nonwoven fabric containing a low crystalline polypropylene satisfying the following (a) to (f) (hereinafter also simply referred to as a "low crystalline polypropylene"); and a mixed fiber spunbonded nonwoven fabric disposed on at least one surface of the elastic nonwoven fabric (hereinafter also simply referred to as a "mixed fiber spunbonded nonwoven fabric"), wherein the mixed fiber spunbonded nonwoven fabric contains a long fiber of a thermoplastic elastomer (A) and a long fiber of a thermoplastic elastomer (B) other than the thermoplastic elastomer (A) in a ratio of 10 to 90% by mass:90 to 10% by mass ((A):(B), with the proviso that (A)+(B)=100% by mass):

(a) [mmmm]=20 to 60 mol %;
(b) [rrrr]/(1−[mmmm])≤0.1;
(c) [rmrm]>2.5 mol %;
(d) [mm]×[rr]/[mr]$^2$≤2.0;
(e) weight-average molecular weight (Mw)=10,000 to 200,000; and
(f) molecular weight distribution (Mw/Mn)<4, wherein:
[mmmm] is a mesopentad fraction;
[rrrr] is a racemic pentad fraction;
[rmrm] is a racemic meso racemic mesopentad fraction; and
[mm], [rr] and [mr] are triad fractions.

Since the mixed fiber spunbonded nonwoven fabric is disposed on at least one surface of the elastic nonwoven fabric in the multilayer nonwoven fabric of the invention, the adhesion of the multilayer nonwoven fabric to members such as various rotating devices in an apparatus used in an embossing step and the like can be prevented, which provides excellent moldability. Since the spunbonded nonwoven fabric disposed on at least one surface of the elastic nonwoven fabric includes a specific mixed fiber, the multilayer nonwoven fabric is less sticky and excellent in stretchability. Further, the multilayer nonwoven fabric of the invention has excellent low-temperature heat sealability.

The multilayer nonwoven fabric of the invention preferably has a structure in which at least a mixed fiber spunbonded nonwoven fabric is disposed on a surface brought into contact with rotating equipment attached to a nonwoven fabric producing apparatus, and more preferably has a structure in which a mixed fiber spunbonded nonwoven fabric is disposed on each of both surfaces of an elastic nonwoven fabric.

The multilayer nonwoven fabric of the invention usually has a basis weight of 360 g/m² or less, preferably 240 g/m² or less, more preferably 150 g/m² or less, and further preferably from 120 g/m² to 15 g/m². The basis weight can be measured by a method used in Examples described later.

The compositional ratio of the elastic nonwoven fabric to the mixed fiber spunbonded nonwoven fabric may be appropriately determined according to various applications. Usually, the elastic nonwoven fabric:mixed fiber spunbonded nonwoven fabric (basis weight ratio) is in the range of 10:90 to 90:10, preferably in the range of 20:80 to 80:20, and more preferably in the range of 20:80 to 50:50. In a case in which two or more elastic nonwoven fabrics (or mixed fiber spunbonded nonwoven fabrics) exist, the basis weight of the elastic nonwoven fabrics (or mixed fiber spunbonded nonwoven fabrics) is the total of the basis weights of the two or more elastic nonwoven fabrics.

The multilayer nonwoven fabric of the invention usually has residual strain of 25% or less in at least one direction, and preferably 22% or less. In a case in which the multilayer nonwoven fabric has residual strain of 25% or less in at least one direction, the multilayer nonwoven fabric has good stretchability. The residual strain can be measured by a method used in Examples described later.

The multilayer nonwoven fabric of the invention usually has a maximum load elongation of 50% or more in at least one direction, and preferably 100% or more. The maximum load elongation can be measured by a method used in Examples described later.

In a case in which the multilayer nonwoven fabric of the invention has a basis weight of 60 g, the multilayer nonwoven fabric has stress at 50% extending of preferably 1.5 N/50 mm or less, more preferably 1.3 N/50 mm or less, and further preferably 1.2 N/50 mm or less. Stress at 50% recovering is preferably 0.30 N/50 mm or more, more preferably 0.32 N/50 mm or more, and further preferably 0.35 N/50 mm or more. The stress at 50% extending and the stress at 50% recovering differ from stretch characteristics (stress at 50% extending/stress at 50% recovering), and tend to change depending on the basis weight of the multilayer nonwoven fabric, and tend to be increased as the basis weight is increased.

The multilayer nonwoven fabric of the invention has stretch characteristics (stress at 50% extending/stress at 50% recovering) of preferably 3.0 or less, more preferably 2.9 or less, and further preferably 2.8 or less. As the value of the stretch characteristics is smaller, the stretch characteristics are more excellent. The stretch characteristics can be measured by a method used in Examples described later.

The multilayer nonwoven fabric of the invention has low-temperature heat sealability of preferably 10 N/50 mm or more, more preferably 12 N/50 mm or more, and further preferably 15N/50 mm or more. The low-temperature heat sealability can be measured by a method used in Examples described later.

<Elastic Nonwoven Fabric>

The elastic nonwoven fabric constituting the multilayer nonwoven fabric of the invention contains a low crystalline polypropylene satisfying (a) to (f) described later (hereinafter also simply referred to as a low crystalline polypropylene). From the viewpoint of effectively achieving the object of the invention, the proportion of the low crystalline polypropylene in the elastic nonwoven fabric is preferably 60% by mass or more, more preferably 70% by mass or more, and further preferably 80% by mass or more.

Examples of the form of the elastic nonwoven fabric include composite fibers such as sheath-core type composite fibers and side-by-side type composite fibers, and mixed fibers. The elastic nonwoven fabric may contain a resin other than the low crystalline polypropylene. The resin other than the low crystalline polypropylene constituting the elastic nonwoven fabric is not particularly limited, but from the viewpoint of stretch characteristics, it is preferable to use a thermoplastic elastomer. As the thermoplastic elastomer, various known thermoplastic elastomers can be used, and two or more kinds of thermoplastic elastomers may be used in combination. Examples of the thermoplastic elastomer include: a styrene elastomer typified by a block copolymer composed of at least one polymer block composed of at least one aromatic vinyl compound such as styrene, which is typified by a polystyrene-polybutadiene-polystyrene block copolymer (referred to SBS), a polystyrene-polyisoprene-polystyrene block copolymer (referred to SIS), and hydrogenated products thereof, e.g., a polystyrene-polyethylene-butylene-polystyrene block copolymer (referred to SEBS) and a polystyrene-polyethylene-propylene-polystyrene block copolymer (referred to SEPS), and at least one polymer block composed of a conjugated diene compound such as butadiene or isoprene, or a hydrogenated product thereof; a polyester elastomer typified by a block copolymer composed of a high crystalline aromatic polyester and a noncrystalline aliphatic polyether, a polyamide elastomer typified by a block copolymer composed of a crystalline polyamide having a high melting point and a noncrystalline polyether or polyester having a low glass transition temperature (Tg); a thermoplastic polyurethane elastomer (TPU) typified by a block copolymer containing a hard segment composed of polyurethane, and a soft segment composed of polycarbonate polyol, ether polyol, caprolactone polyester or adipate polyester; a polyolefin elastomer of a simple body typified by a noncrystalline or low-crystalline ethylene•α-olefin random copolymer, a propylene•α-olefin random copolymer or a propylene•ethylene•α-olefin random copolymer, or a polyolefin elastomer of a mixture of the noncrystalline or low-crystalline random copolymer with a propylene homopolymer, or a polyolefin elastomer of a mixture of the noncrystalline or low-crystalline random copolymer with a crystalline polyolefin such as a copolymer of propylene and a small amount of an α-olefin, a high density polyethylene, and a middle density polyethylene; a polyvinyl chloride elastomer; and a fluorine elastomer.

In the invention, the elastic nonwoven fabric refers to a nonwoven fabric having an elastic recovering property in a case in which stress is released after drawing.

The elastic nonwoven fabric can be produced by various known methods. Specific examples thereof include a spunbond method, a melt blow method, and a flash spinning method. Among the elastic nonwoven fabrics, a spunbonded nonwoven fabric obtained by the spunbond method or a meltblown nonwoven fabric obtained by the melt blow method is preferable.

The elastic nonwoven fabric usually has a basis weight of 120 g/m$^2$ or less, preferably 80 g/m$^2$ or less, more preferably 50 g/m$^2$ or less, and further preferably from 40 g/m$^2$ to 2 g/m$^2$.

The fiber constituting the elastic nonwoven fabric usually has a fiber diameter of 50 μm or less, preferably 40 μm or less, and more preferably 30 μm or less.

[Low Crystalline Polypropylene]

The low crystalline polypropylene is a polymer satisfying the following requirements (a) to (f).

(a) [mmmm]=20 to 60 mol %:

In a case in which the mesopentad fraction [mmmm] of the low crystalline polypropylene is 20 mol % or more, the occurrence of stickiness is suppressed, and in a case in which the mesopentad fraction is 60 mol % or less, the degree of crystallinity does not become too high, so that the elastic recoverability is good. The mesopentad fraction [mmmm] is preferably from 30 to 50 mol %, and more preferably from 40 to 50 mol %.

The mesopentad fraction [mmmm], and the racemic pentad fraction [rrrr] and the racemic meso racemic mesopentad fraction [rmrm] described later are the meso fraction, the racemic fraction and the racemic meso racemic meso fraction, respectively, of pentad units in polypropylene molecule chains measured with respect to methyl group signals in a $^{13}$C-NMR spectrum in accordance with the method proposed in A. Zambelli, et al., "Macromolecules, 6, 925 (1973)". The larger the mesopentad fraction [mmmm] is, the higher the stereoregularity is. Triad fractions [mm], [rr] and [mr], which will be described later, are also calculated by the above method.

A $^{13}$C-NMR spectrum can be measured using the following apparatus under the following conditions according to the assignment of peaks proposed in A. Zambelli, et al., "Macromolecules, 8, 687 (1975)".

Apparatus: JNM-EX 400 $^{13}$C-NMR apparatus, manufactured by JEOL Ltd.
Method: Complete proton decoupling method
Concentration: 220 mg/ml
Solvent: 90:10 (by volume) mixed solvent of 1,2,4-trichlorobenzene and deuterated benzene
Temperature: 130° C.
Pulse width: 45°
Pulse interval: 4 seconds
Integration: 10000 times
[Calculation Formulae]
M=m/S×100
R=γ/S×100
S=Pββ+Pαβ+Pαγ
S: signal intensity of methyl carbon atoms in side chains of all propylene units
Pββ: 19.8 to 22.5 ppm
Pαβ: 18.0 to 17.5 ppm
Pαγ: 17.5 to 17.1 ppm
Γ: racemic pentad chains: 20.7 to 20.3 ppm
m: mesopentad chains: 21.7 to 22.5 ppm
(b)[rrrr]/(1−[mmmm])≤0.1

The [rrrr]/[1−mmmm] value is obtained from the above pentad fractions. This value is an index of the uniformity of regularity distribution in the low crystalline polypropylene. As this value increases, the polymer is a mixture of high-regularity polypropylene and atactic polypropylene as is the case for conventional polypropylene produced using the existing catalyst system, which causes stickiness.

In a case in which the low crystalline polypropylene has [rrrr]/(1−[mmmm]) of 0.1 or less, the stickiness of the obtained elastic nonwoven fabric is suppressed. From such a viewpoint, [rrrr]/(1−[mmmm]) is preferably 0.05 or less, and more preferably 0.04 or less.

(c) [rmrm]>2.5 mol %;
(d) [mm]×[rr]/[mr]²≤2.0;

In a case in which the racemic meso racemic meso fraction [rmrm] of the low crystalline polypropylene exceeds 2.5 mol %, the randomness of the low crystalline polypropylene is increased and the elastic recoverability of the elastic nonwoven fabric is further improved. [rmrm] is preferably 2.6 mol % or more, and more preferably 2.7 mol % or more. The upper limit thereof is usually about 10 mol %.

(d)[mm]×[rr]/[mr]²≤2.0

[mm]×[rr]/[mr]² represents an index of the randomness of the low crystalline polypropylene. In a case in which this value is 2.0 or less, the elastic nonwoven fabric has sufficient elastic recoverability and suppressed stickiness. As [mm]×[rr]/[mr]² becomes closer to 0.25, the randomness is increased. From the viewpoint of obtaining the above sufficient elastic recoverability, [mm]×[rr]/[mr]² is preferably from more than 0.25 to 1.8 or less, and more preferably from 0.5 to 1.5.

(e) weight-average molecular weight (Mw)=10,000 to 200,000; and

In a case in which the weight-average molecular weight of the low crystalline polypropylene is 10,000 or more, the low crystalline polypropylene exhibits a moderately low viscosity so as to suppress filament breakage during the production of the elastic nonwoven fabric. In a case in which the weight-average molecular weight of the low crystalline polypropylene is 200,000 or less, the low crystalline polypropylene exhibits a moderately high viscosity so as to achieve improved spinnability. This weight-average molecular weight is preferably from 30,000 to 150,000, and more preferably from 50,000 to 150,000. The measurement method of the weight-average molecular weight will be described later.

(f) molecular weight distribution (Mw/Mn)<4,

In a case in which the molecular weight distribution (Mw/Mn) of the low crystalline polypropylene is less than 4, the occurrence of the stickiness of the elastic nonwoven fabric is suppressed. The molecular weight distribution is preferably 3 or less.

The weight-average molecular weight (Mw) is a weight-average molecular weight in terms of polystyrene measured by the gel permeation chromatography (GPC) method under the following apparatus and conditions. The molecular weight distribution (Mw/Mn) is a value calculated from the number average molecular weight (Mn) measured in the similar manner and the weight-average molecular weight (Mw).

[GPC Measuring Apparatus]
Column: TOSOGMHHR-H(S)HT
Detector: RI detector for liquid chromatogram WATERS 150 C
[Measurement Conditions]
Solvent: 1,2,4-trichlorobenzene
Measurement temperature: 145° C.
Flow rate: 1.0 ml/min
Sample concentration: 2.2 mg/ml
Injection volume: 160 µl
Calibration curve: UniversalCalibration
Analysis program: HT-GPC (Ver. 1.0)

It is preferable that the low crystalline polypropylene further satisfy the following (g).

(g) Using a differential scanning calorimeter (DSC), the polymer is held at −10° C. for 5 minutes under a nitrogen atmosphere and is thereafter heated at a temperature increasing rate of 10° C./min. The obtained melting endothermic curve shows a melting point (Tm-D) of 0° C. to 120° C. wherein the melting point is defined as the peak top temperature of the peak observed on the highest temperature side of the curve.

In a case in which the melting point (Tm-D) of the low crystalline polypropylene is 0° C. or higher, the occurrence of the stickiness of the elastic nonwoven fabric is suppressed.

In a case in which the melting point is 120° C. or less, sufficient elastic recoverability is obtained. From this viewpoint, the melting point (Tm-D) is more preferably from 0° C. to 100° C., and further preferably from 30° C. to 100° C.

The melting point (Tm-D) can be determined by using a differential scanning calorimeter (DSC-7, manufactured by Perkin Elmer), holding 10 mg of a sample at −10° C. under a nitrogen atmosphere for 5 minutes, thereafter heating the sample at a temperature increase rate of 10° C./min to record a melting endothermic curve, and determining the temperature as the peak top of the peak observed on the highest temperature side of the curve.

The low crystalline polypropylene can be synthesized using a homogeneous catalyst referred to as a so-called metallocene catalyst as described, for example, in International Publication No. 2003/087172.

The low crystalline polypropylene may contain various known additives such as an antioxidant, a heat stabilizer, a weathering stabilizer, an antistatic agent, a slip agent, an antifogging agent, a lubricant, a dye, a pigment, a natural oil, a synthetic oil, and wax as optional components while still achieving the object of the invention.

<Mixed Fiber Spunbonded Nonwoven Fabric>

The mixed fiber spunbonded nonwoven fabric constituting the multilayer nonwoven fabric of the invention is a mixed fiber spunbonded nonwoven fabric containing long fibers of the thermoplastic elastomer (A) and long fibers of the thermoplastic resin (B) other than (A) at a ratio of 10 to 90% by mass:90 to 100/by mass ((A):(B), with the proviso that (A)+(B)=100% by mass).

From the viewpoint of stretchability and flexibility, the proportion of the long fibers of the thermoplastic elastomer (A) in the mixed fiber spunbonded nonwoven fabric is preferably 20% by mass or more, and more preferably 30% by mass or more. From the viewpoint of processability (sticky resistance), the proportion of the long fibers of the thermoplastic elastomer (A) in the mixed fiber spunbonded nonwoven fabric is preferably 70% by mass or less, and more preferably 60% by mass or less.

The fiber diameters (average value) of the long fibers of each of the thermoplastic elastomer (A) and the thermoplastic resin (B) that form the mixed fiber spunbonded nonwoven fabric are usually 50 μm or less, preferably 40 μm or less, and more preferably 30 μm or less. The fiber diameter of the long fibers of the thermoplastic elastomer (A) and the fiber diameter of the long fibers of the thermoplastic resin (B) may be the same or different.

In applications for sanitary materials such as diapers, from the viewpoint of flexibility and air breathability, the mixed fiber spunbonded nonwoven fabric generally has a basis weight of 120 g/m² or less, preferably 80 g/m² or less, more preferably 50 g/m² or less, and further preferably from 40 g/m² to 15 g/m² in the total multilayer.

[Thermoplastic Elastomer (A)]

As the thermoplastic elastomer (A), various known thermoplastic elastomers can be used. One kind of the thermoplastic elastomers may be used alone, or two or more kinds of the thermoplastic elastomers may be used in combination.

Examples of the thermoplastic elastomer (A) include a styrene elastomer, a polyester elastomer, a polyamide elastomer, a thermoplastic polyurethane elastomer, a polyolefin elastomer, a vinyl chloride elastomer, and a fluorine elastomer.

The styrene elastomer is an elastomer typified by a polystyrene-polybutadiene-polystyrene block copolymer (SBS), a polystyrene-polyisoprene-polystyrene block copolymer (SIS), and a polystyrene-polyethylene-butylene-polystyrene block copolymer (SEBS), and a polystyrene-polyethylene propylene-polystyrene block copolymer (SEPS) which are hydrogenation products thereof. The styrene elastomer is a block copolymer composed of at least one polymer block composed of an aromatic vinyl compound such as styrene and at least one conjugated diene compound such as butadiene or isoprene, or a hydrogenated product thereof. Examples of the styrene elastomer include KRATON polymer (trade name, manufactured by Shell Chemical Co.), SEPTON (trade name, manufactured by Kuraray Co., Ltd.), TUFTEC (trade name, manufactured by Asahi Chemical Industry Co., Ltd.), and LEOSTOMER (trade name, manufactured by RIKEN TECHNOS CORPORATION).

The polyester elastomer is an elastomer typified by a block copolymer composed of a highly crystalline aromatic polyester and a noncrystalline aliphatic polyether. The polyester elastomer is sold under the trade names of, for example, HYTREL (trade name, manufactured by EI du Pont de Nemours and Company) and PELPRENE (trade name, manufactured by Toyobo Co., Ltd.).

The polyamide elastomer is an elastomer typified by a block copolymer composed of crystalline polyamide having a high melting point and a noncrystalline polyether or polyester having a low glass transition temperature (Tg). The polyamide elastomer is sold under the trade name of PEBAX (trade name, Atofina Japan Ltd.), for example.

The thermoplastic polyurethane elastomer is an elastomer typified by a block copolymer in which a hard segment is composed of polyurethane and a soft segment is composed of a polycarbonate polyol, an ether polyol, a caprolactone polyester, or an adipate polyester and the like.

The polyolefin elastomer is an elastomer containing a simple body such as a noncrystalline or low crystalline ethylene•α-olefin random copolymer, a propylene•α-olefin random copolymer, or a propylene•ethylene•α-olefin random copolymer; or an elastomer as a mixture of the noncrystalline or low crystalline random copolymer with a propylene homopolymer; or an elastomer as a mixture of the noncrystalline or low crystalline random copolymer with crystalline polyolefin such as a copolymer of propylene and a small amount of an α-olefin, a high density polyethylene, and a medium density polyethylene. The polyolefin elastomer is sold under the trade names of, for example, TAFMER (trade name, manufactured by Mitsui Chemicals, Inc.), Engage (trade name, manufactured by DuPont Dow Elastomers) which is an ethylene-octene copolymer, CATALLOY containing a crystalline olefin copolymer (trade name, manufactured by Montel Co., Ltd.), and Vistamaxx (trade name, manufactured by Exxon Mobil Chemical Co., Ltd.), and the like.

The vinyl chloride elastomer is sold under the trade names such as Leonyl (trade name, manufactured by Riken Technos Co., Ltd.), and POSMYL (trade name, manufactured by Shin-Etsu Polymer Co., Ltd.).

Among these thermoplastic elastomers, the thermoplastic polyurethane elastomer and the polyolefin elastomer are preferable, and the thermoplastic polyurethane elastomer is more preferable from the viewpoint of stretchability and processability.

(Thermoplastic Polyurethane Elastomer)

Among the thermoplastic polyurethane elastomers, thermoplastic polyurethane elastomers having a solidification starting temperature of 65° C. or higher, preferably 75° C. or higher, and most preferably 85° C. or higher are preferable. The solidification starting temperature is preferably 195° C. or lower. Here, the solidification starting temperature is a value measured using a differential scanning calorimeter (DSC), and is the starting temperature of an exothermic peak derived from the solidification of the thermoplastic polyurethane elastomer occurring in a case in which the temperature of the thermoplastic polyurethane elastomer is decreased at a rate of 10° C./min after the temperature of the thermoplastic polyurethane elastomer is increased at 10° C./min to 230° C. and kept at 230° C. for 5 min. In a case in which the solidification starting temperature is 65° C. or higher, it is possible to suppress defective molding such as fusion of fibers, filament breakage, massed resin in obtaining a mixed fiber spunbonded nonwoven fabric, and also it is possible to prevent the molded mixed fiber spunbonded nonwoven fabrics from being wound around the emboss roller in thermal emboss processing. The obtained mixed fiber spunbonded nonwoven fabrics have less stickiness, and are suitably used as materials that come in contact with skin such as clothes, hygiene materials, and materials of sporting goods. On the other hand, by setting the solidification starting temperature to 195° C. or lower, the molding processability can be improved. The solidification starting temperature of the molded fiber tends to be higher than the solidification starting temperature of the thermoplastic polyurethane elastomer used for the fiber.

In order to adjust the solidification starting temperature of the thermoplastic polyurethane elastomer to 65° C. or higher, it is necessary to select a polyol, an isocyanate compound, and a chain extender each having an optimum chemical structure, which are used as raw materials for the thermoplastic polyurethane elastomer, and to adjust a hard segment amount. The term "hard segment amount" as used herein is a mass percent value (% by mass) determined by dividing the total mass of the isocyanate compound and the chain extender used is in the production of the thermoplastic polyurethane elastomer by the total amount of the polyol, the isocyanate compound, and the chain extender, and multiplying the resulting value by 100. The hard segment amount is preferably from 20% by mass to 60% by mass, more preferably from 22% by mass to 50% by mass, and further preferably from 25% by mass to 48% by mass.

The thermoplastic polyurethane elastomer has the number of particles as components insoluble in a polar solvent of preferably 3,000,000 particles (3,000,000 particles/g) or less, more preferably 2,500,000 particles/g or less, and further preferably 2,000,000 particles/g or less with respect to 1 g of the thermoplastic polyurethane elastomer. Here, the components insoluble in the polar solvent in the thermoplastic polyurethane elastomer are mainly agglomerates such as fish eye and gel occurring during the production of the thermoplastic polyurethane elastomer. Examples of components causing the occurrence of the components insoluble in the polar solvent include components derived from hard segment agglomerates of the thermoplastic polyurethane elastomer, components obtained by crosslinking the hard segment and/or the soft segment with an allophanate bond or a biuret bond and the like, and components produced by a chemical reaction between raw materials.

The number of particles as the components insoluble in the polar solvent is determined by dissolving the thermoplastic polyurethane elastomer in a dimethylacetamide solvent (hereinafter abbreviated as "DMAC") and measuring the insoluble components by means of a particle size distribution measuring apparatus equipped with a 100 μm aperture utilizing a pore electrical resistance method. Using the apparatus equipped with a 100 μm aperture, the number of particles of from 2 to 60 μm can be measured in terms of uncrosslinked polystyrene.

By setting the number of particles as the components insoluble in the polar solvent to 3,000,000 particles/g or less, problems such as an increase in a distribution of a fiber diameter, and filament breakage in spinning can be further suppressed in the solidification starting temperature range of the thermoplastic polyurethane elastomer. The thermoplastic polyurethane elastomer having a low content of the components insoluble in the polar solvent can be obtained by conducting a polymerization reaction of a polyol, an isocyanate compound, and a chain extender, followed by filtration.

From the viewpoint of suppressing mingling of bubbles into a strand or occurrence of filament breakage in the molding of nonwoven fabrics using a large-size spunbonding molding machine, the thermoplastic polyurethane elastomer has a water content of preferably 350 ppm or less, more preferably 300 ppm or less, and further preferably 150 ppm or less.

From the viewpoint of stretchability, in the thermoplastic polyurethane elastomer, a total amount (a) of fusion heat determined from an endothermic peak at a peak temperature in a range of 90° C. to 140° C. as measured by a differential scanning calorimeter (DSC) and a total amount (b) of fusion heat determined from an endothermic peak at a peak temperature of from higher than 140° C. to 220° C. or lower preferably satisfy the following formula (I), more preferably satisfy the following formula (II), and further preferably satisfy the following formula (III).

$$a/(a+b) \leq 0.8 \tag{I}$$

$$a/(a+b) \leq 0.7 \tag{II}$$

$$a/(a+b) \leq 0.55 \tag{II}$$

Here, "a/(a+b)" means a ratio (unit: %) of the amount of fusion heat of the hard domain of the thermoplastic polyurethane elastomer. In a case in which the ratio of the amount of fusion heat of the hard domain of the thermoplastic polyurethane elastomer is 80% or less, the strength and stretchability of the fiber, particularly the fiber and nonwoven fabric in the mixed fiber spunbonded nonwoven fabric are improved. In the invention, the lower limit of the ratio of the amount of fusion heat of the hard domain of the thermoplastic polyurethane elastomer is preferably about 0.1%.

The thermoplastic polyurethane elastomer preferably has a melt viscosity of 100 Pa·s to 3000 Pa·s under conditions of a temperature of 200° C. and a shear rate of 100 sec$^{-1}$, more preferably from 200 Pa·s to 2000 Pa·s, and further preferably from 1000 Pa·s to 1500 Pa·s. Herein, the melt viscosity is a value measured by a capirograph (manufactured by Toyo Seiki Co., Ltd., nozzle length: 30 mm, diameter: 1 mm).

The thermoplastic polyurethane elastomer having such characteristics can be obtained by, for example, the production method described in JP-A No. 2004-244791.

The mixed fiber spunbonded nonwoven fabric molded by using the thermoplastic polyurethane elastomer is excellent in tactile sensation and therefore can be preferably used for applications that come in contact with skin such as a sanitary material. The thermoplastic polyurethane based elastomer hardly causes clogging of a filter that is mounted in an extruder in order to filter impurities and the like, and reduces the frequency of adjustment and maintenance for equipment, which is industrially preferable.

(Polyolefin Elastomer)

Among the polyolefin elastomers, noncrystalline or low crystalline polyolefin elastomers are preferable, and an ethylene•α-olefin copolymer which is a copolymer of noncrystalline or low crystalline ethylene and one or more α-olefins having 3 to 20 carbon atoms such as propylene, 1-butene, 1-pentene, 1-hexene, 4-methyl-1-pentene, 1-heptene, 1-octene, and 1-decene, and a propylene•α-olefin copolymer which is a copolymer of noncrystalline or low crystalline propylene and one or more α-olefins having 2 to 20 carbon atoms (excluding 3 carbon atoms) such as ethylene, 1-butene, 1-pentene, 1-hexene, 4-methyl-1-pentene, 1-heptene, 1-octene, and 1-decene are more preferable. The noncrystalline or low crystalline polyolefin elastomer is, for example, a polyolefin elastomer having a degree of crystallinity of 20% or less (including 0%) as measured by X-ray diffraction.

Specific examples of the noncrystalline or low crystalline ethylene•α-olefin copolymer include an ethylene•propylene random copolymer, and an ethylene•1-butene random copolymer. The melt flow rate (MFR) of the ethylene•α-olefin copolymer is not particularly limited as long as the ethylene•α-olefin copolymer has spinnability, but MFR (ASTM D1238 190° C., load: 2160 g) and MFR (ASTM D1238 230° C., load: 2160 g) are usually in the range of from 1 g/10 min to 1000 g/10 min, preferably from 5 g/10 min to 500 g/10 min, and more preferably from 10 g/10 min to 100 g/10 min.

Specific examples of the noncrystalline or low crystalline propylene•α-olefin copolymer include a propylene•ethylene random copolymer, a propylene-ethylene-1-butene random copolymer, and a propylene 1-butene random copolymer. MFR of the propylene•α-olefin copolymer is not particularly limited as long as the propylene•α-olefin copolymer has spinnability, but MFR (ASTM D1238 230° C., load: 2160 g) is usually from 1 g/10 min to 1000 g/10 min, preferably from 5 g/10 min to 500 g/10 min, and more preferably from 10 g/10 min to 100 g/10 min.

The polyolefin elastomer may be a single body of a copolymer of noncrystalline or low crystalline polymer, and may also be a composition obtained by mixing a propylene homopolymer, a copolymer of propylene and a small amount of α-olefin, or crystalline polyolefin such as a high density polyethylene or a medium density polyethylene in an amount of about 1 to about 40% by mass with the noncrystalline or low crystalline polymer.

A composition that is particularly preferable as the polyolefin elastomer is an elastomer composition containing a polypropylene resin composition containing 1 to 40% by mass of isotactic polypropylene (i) and 60 to 99% by mass of a propylene•ethylene•α-olefin copolymer (ii) (a copolymer of 45 to 89 mol % of propylene, 10 to 25 mol % of ethylene, and α-olefin having 4 to 20 carbon atoms, the amount of copolymerized α-olefin having 4 to 20 carbon atoms does not exceed 30 mol %).

[Thermoplastic Resin (B)]

As the thermoplastic resin (B), various known thermoplastic resins other than the thermoplastic elastomer (A) can be used, and the thermoplastic resins may be used alone, or in combination of two or more.

The thermoplastic resin (B) is a resinous polymer different from the thermoplastic elastomer (A), and is usually a crystalline polymer having a melting point (Tm) of 100° C. or higher, or a noncrystalline polymer having a glass transition temperature of 100° C. or higher. As the thermoplastic resin (B), the crystalline thermoplastic resin is preferable.

Among the thermoplastic resins (B), it is preferable to use a thermoplastic resin (extensible thermoplastic resin) having a maximum point elongation of 50% or more, preferably 70% or more, and more preferably 100% or more and having quite low elastic recoverability in a case of a spunbonded nonwoven fabric obtained by a known production method. A multilayer nonwoven fabric produced by using a mixed fiber spunbonded nonwoven fabric obtained by mixing long fibers of such a thermoplastic resin (B) with long fibers of the thermoplastic elastomer (A) can exhibit bulkiness due to drawing, and have improved tactile feeling and an extension stop function. The upper limit of the maximum point elongation of the spunbonded nonwoven fabric made of the thermoplastic resin (B) is not necessarily limited, but it is usually 300% or less.

Specific examples of the thermoplastic resin (B) include polyolefins which are homopolymers or copolymers of α-olefins including ethylene, propylene, 1-butene, 1-hexene, 4-methyl-1-pentene, and 1-octene, including polyolefins such as high pressure low density polyethylene, linear low density polyethylene (so-called LLDPE), high density polyethylene (so-called HDPE), polypropylene (propylene homopolymer), polypropylene random copolymer, poly 1-butene, poly 4-methyl-1-pentene, ethylene-propylene random copolymer, ethylene 1-butene random copolymer and propylene 1-butene random copolymer; polyesters (polyethylene terephthalate, polybutylene terephthalate, polyethylene naphthalate etc.); polyamide (nylon-6, nylon-66, polymetaxyleneadipamide, etc.); polyvinyl chloride; polyimide; ethylene•vinyl acetate copolymer; ethylene•vinyl acetate-vinyl alcohol copolymer; ethylene(meth)acrylic acid copolymer; ethylene-acrylic ester-carbon monoxide copolymer; polyacrylonitrile; polycarbonate; polystyrene; ionomer, and mixtures of the thermoplastic resins. Of these, polyolefin, polyethylene terephthalate, and polyamide are preferable.

Among these thermoplastic resins (B), from the viewpoint of spinning stability during molding and drawing processability of the nonwoven fabric, polyolefin is more preferable, and high-pressure low density polyethylene, linear low density polyethylene (so-called LLDPE), high density polyethylene, and propylene polymers such as polypropylene and a polypropylene random copolymer are further preferable.

The propylene polymer is preferably a propylene homopolymer or a copolymer of propylene and a very small amount of one or two or more α-olefins having 2 or more carbon atoms (excluding 3 carbon atoms), and preferably 2 to 8 carbon atoms (excluding 3 carbon atoms) such as ethylene, 1-butene, 1-pentene, 1-hexene, 1-octene, and 4-methyl-1-pentene, having a melting point (Tm) of 155° C. or higher, and preferably 157° C. to 165° C.

The melt flow rate (MFR: ASTMD-1238, 230° C., load: 2160 g) of the propylene polymer is not particularly limited as long as the propylene polymer can be melt-spun. The melt flow rate of the propylene polymer is usually 1 g/10 min to 1000 g/10 min, more preferably 5 g/10 min to 500 g/10 min, and more preferably 10 g/10 min to 100 g/10 min.

The ratio Mw/Mn of the weight-average molecular weight (Mw) of the propylene polymer to the number average molecular weight (Mn) is usually 1.5 to 5.0. Mw/Mn is preferably in the range of 1.5 to 3.0 in that fibers having good spinnability and excellent fiber strength can be obtained. Mw and Mn can be measured by a known method using GPC (gel permeation chromatography).

From the viewpoint of further improving the drawing processing properties of the obtained multilayer nonwoven fabric, it is preferable that the thermoplastic resin (B) is an olefinic polymer composition obtained by adding HDPE to a propylene polymer. In this case, the ratio of HDPE is preferably 1% by mass to 20% by mass, more preferably 2% by mass to 15% by mass, and further preferably 4% by mass to 10% by mass based on 100% by mass of the total amount of the propylene polymer and HDPE.

The type of HDPE to be added to the propylene polymer is not particularly limited, but HDPE usually has a density is 0.94 g/cm$^3$ to 0.97 g/cm$^3$, preferably 0.95 g/cm$^3$ to 0.97 g/cm$^3$, and more preferably 0.96 g/cm$^3$ to 0.97 g/cm$^3$. HDPE has a melt flow rate (MFR: ASTMD-1238, 190° C., load: 2160 g), which is not particularly limited as long as it has spinnability, of usually 0.1 to 100 g/10 min, preferably 0.5 to 50 g/10 min, and more preferably 1 to 30 g/10 min from the viewpoint of exhibiting extension properties. In the invention, good spinnability means that filament breakage is not caused and filament fusion is not caused during discharging from a spinning nozzle and during drawing.

(Additive)

Various stabilizers such as a heat stabilizer and a weathering stabilizer, an antistatic agent, a slip agent, an antifogging agent, a lubricant, a dye, a pigment, a natural oil, a synthetic oil, and wax and the like can be added to the elastic nonwoven fabric and the mixed fiber spunbonded nonwoven fabric if necessary.

(Other Layers)

The multilayer nonwoven fabric of the invention may have one or more layers other than the elastic nonwoven fabric and the mixed fiber spunbonded nonwoven fabric depending on applications.

Specific examples of the other layer include a knitted fabric, a woven fabric, a nonwoven fabric other than the elastic nonwoven fabric and the mixed fiber spunbonded nonwoven fabric, and a film. A method of further stacking (adhering) another layer on the multilayer nonwoven fabric of the invention is not particularly limited, and various method such as a thermal fusion method (such as thermal embossing or ultrasonic fusion), a mechanical confounding method (such as needle punch or water jet), a method of using an adhesive (such as a hot melt adhesive or a urethane adhesive), and extrusion laminating may be employed.

Examples of nonwoven fabrics other than the elastic nonwoven fabric and the mixed fiber spunbonded nonwoven fabric, included in the multilayer nonwoven fabric of the invention include various known nonwoven fabrics such as a spunbonded nonwoven fabric, a meltblown nonwoven fabric, a wet nonwoven fabric, a dry nonwoven fabric, a dry pulp nonwoven fabric, a flash spun nonwoven fabric, and a split non-woven fabric. The nonwoven fabric may be a stretchable nonwoven fabric or a nonstretchable nonwoven fabric. Herein, the nonstretchable nonwoven fabric refers to a nonwoven fabric which does not cause stress at recovering after extending in MD (machine direction of the nonwoven fabric, longitudinal direction) or CD (direction perpendicular to the machine direction of the nonwoven fabric, lateral direction).

The film included in the multilayer nonwoven fabric of the invention is preferably an air breathable (moisture permeable) film from the viewpoint of maintaining air breathability and hydrophilicity which are features of the multilayer nonwoven fabric of the invention. Examples of the air breathable film include various known air breathable films such as a film made of moisture permeable thermoplastic elastomer (such as a polyurethane elastomer, a polyester elastomer, or a polyamide elastomer), and a porous film obtained by drawing a film made of a thermoplastic resin containing inorganic fine particles or organic fine particles to create pores in the film. As the thermoplastic resin used for the porous film, polyolefins such as high pressure low density polyethylene, linear low density polyethylene (so-called LLDPE), high density polyethylene, polypropylene, a polypropylene random copolymer, and combinations thereof are preferable. In a case in which it is not necessary to maintain the air breathability and hydrophilicity of the multilayer nonwoven fabric, thermoplastic resin films made of polyethylene, polypropylene, or combinations thereof and the like may be used.

(Producing Method of Multilayer Nonwoven Fabric)

The multilayer nonwoven fabric of the invention can be produced by a known nonwoven fabric producing method using low crystalline polypropylene as a raw material of an elastic nonwoven fabric, a thermoplastic elastomer (A) and a thermoplastic resin (B) as raw materials of a mixed fiber spunbonded nonwoven fabric, and an additive used if necessary.

As an example of a method of producing a multilayer nonwoven fabric, a method of using a nonwoven fabric producing apparatus having at least two-line spinning devices will be described below.

First, a thermoplastic elastomer (A) and a thermoplastic resin (B) are melted by an extruder provided in a first-line spinning device, introduced to a spinneret (die) fitted with a large number of spinning holes (nozzles) or sheath-core spinning holes if necessary, and discharged. Thereafter, the long fibers composed of the melt-spun thermoplastic elastomer (A) and the long fibers composed of the thermoplastic resin (B) are introduced into a cooling chamber, and cooled by cooling air. The long fibers are then drawn (towed) by drawing air, and the mixed fiber spunbonded nonwoven fabric is deposited on a moving collection surface.

On the other hand, the low crystalline polypropylene is melted by an extruder provided in a second-line spinning device, and introduced into spinning holes having a spinneret (die) having a large number of spinning holes (nozzles). The low crystalline polypropylene is discharged. Thereafter, the long fibers composed of the melt-spun low crystalline polypropylene are introduced into a cooling chamber, and cooled by cooling air. Thereafter, the long fibers are drawn (towed) by drawing air, and deposited on the mixed fiber spunbonded nonwoven fabric, thereby forming an elastic nonwoven fabric.

If necessary, a mixed fiber spunbonded nonwoven fabric may be deposited on the elastic nonwoven fabric by using a third-line spinning device.

The melting temperatures of polymers serving as raw materials for the elastic nonwoven fabric and the mixed fiber spunbonded nonwoven fabric are not particularly limited as long as the temperatures are equal to or higher than the softening temperature or melting temperature of each polymer and lower than the thermal decomposition temperature. The temperature of the spinneret depends on the type of the polymer to be used. For example, in a case in which a thermoplastic polyurethane elastomer or an olefin copolymer elastomer is used as the thermoplastic elastomer (A), and a propylene polymer or an olefin polymer composition of a propylene polymer and HDPE is used as the thermoplastic resin (B), the temperature of the spinneret is usually set to a temperature of from 180° C. to 240° C., preferably from 190 to 230° C., and more preferably from 200 to 225° C.

The temperature of the cooling air is not particularly limited as long as the polymer can be solidified, but it is usually from 5° C. to 50° C., preferably from 10° C. to 40° C., and more preferably from 15° C. to 30° C. A drawing air velocity is usually in the range of from 100 m/min to 10,000 m/min, and preferably from 500 m/min to 10,000 m/min.

The multilayer nonwoven fabric of the invention preferably has a structure in which at least a part of the elastic nonwoven fabric and at least a part of the mixed fiber spunbonded nonwoven fabric are thermally fusion bonded. At this time, at least a part of the elastic nonwoven fabric and at least a part of the mixed fiber spunbonded nonwoven fabric may be compacted with nip rolls before thermal fusion bonding.

The method of thermal fusion bonding is not particularly limited, and it can be selected from various known methods. Examples of prebonding methods include a method of using means such as ultrasonic waves, thermal embossing using embossing rolls, and a method using hot air through. Among these, from the viewpoint that the long fibers are efficiently drawn during drawing, thermal embossing is preferable, and the temperature range thereof is preferably from 60° C. to 115° C.

In a case in which a part of the multilayer is thermally fusion bonded by thermal embossing, the emboss area ratio is usually from 5% to 30%, and preferably from 5% to 20%, and the non-embossed unit area is 0.5 mm$^2$ or more, and preferably from 4 mm$^2$ to 40 mm$^2$. The non-embossed unit area is the maximum area of a quadrangle inscribed in emboss in a non-embossed portion of minimum units surrounded by embossed portions in all directions. Examples of the shape of the mark include a circle, an ellipse, an oval, a square, a rhombus, a rectangle, a square, and continuous shapes based on these shapes.

<Stretchable Multilayer Nonwoven Fabric>

The stretchable multilayer nonwoven fabric of the invention is a multilayer nonwoven fabric having stretchability obtained by drawing the multilayer nonwoven fabric.

The stretchable multilayer nonwoven fabric of the invention can be obtained by drawing the multilayer nonwoven fabric. The drawing method is not particularly limited, and conventionally known methods can be applied. The drawing method may be such that the multilayer nonwoven fabric is drawn partially or entirely. The drawing method may be such that the multilayer nonwoven fabric is drawn uniaxially or biaxially. Examples of the method of drawing the multilayer nonwoven fabric in a machine direction (MD) include a method of passing the partially fusion bonded mixed fibers through two or more pairs of nip rolls. At this time, the partially fusion bonded multilayer nonwoven fabric can be drawn by increasing the rotational speeds of the nip rolls in order in the machine direction. Gear drawing can also be performed using a gear drawing device shown in FIG. 1.

The draw ratio is preferably 50% or more, more preferably 100% or more, and further preferably 200% or more, and preferably 1000% or less, and more preferably 400% or less.

In the case of uniaxial drawing, the above draw ratio is preferably satisfied in the machine direction (MD) or a direction perpendicular thereto (CD). In the case of biaxial drawing, the above draw ratio is preferably satisfied in at least one of the machine direction (MD) or the direction perpendicular thereto (CD).

By drawing at the above draw ratio, all the (long) fibers forming the elastic nonwoven fabric and the mixed fiber spunbonded nonwoven fabric are drawn. The long fibers forming the mixed fiber spunbonded nonwoven fabric layer are plastically deformed to be extended (lengthened) in accordance with the above draw ratio.

Therefore, in a case in which the stress is released after the multilayer nonwoven fabric is drawn, the (long) fibers forming the elastic nonwoven fabric are elastically recovered, and the long fibers forming the mixed fiber spunbonded nonwoven fabric are folded without being elastically recovered. As a result, the multilayer nonwoven fabric exhibits bulkiness. In addition, since the long fibers forming the mixed fiber spunbonded nonwoven fabric become thinner, the long fibers can have improved flexibility and tactile feeling, and an extension stop function.

<Fiber Product>

The fiber product of the invention includes the multilayer nonwoven fabric or the stretchable multilayer nonwoven fabric of the invention. The fiber product is not particularly limited, and examples thereof include absorbent articles such as disposable diapers and sanitary articles, hygiene articles such as sanitary masks, medical articles such as bandages, clothing materials, and packaging materials. The fiber product of the invention preferably includes the multilayer nonwoven fabric or the stretchable multilayer nonwoven fabric of the invention as an elastic member.

EXAMPLES

Hereinafter, the invention will be more specifically described with reference to Examples, but the invention is not limited to these Examples. Physical property values and the like in Examples and Comparative Examples were measured by the following methods.

(1) Basis Weight [g/m$^2$]

Six test pieces of 200 mm (machine direction: MD)×50 mm (lateral direction: CD) were sampled from a nonwoven fabric simple body or a multilayer nonwoven fabric. Three sampling points were arbitrarily selected for both MD and CD (6 points in total). Subsequently, the mass (g) of each of the sampled test pieces was measured using a scale electric balance (manufactured by Kensei Co., Ltd.). The average value of the masses of the test pieces was determined. The determined average value was converted to the mass (g) per 1 m$^2$ to the first decimal place to give a basis weight [g/m$^2$] of each sample.

(2) Moldability

Embossing rolls were run for 5 minutes in an embossing step, to confirm an adhesion state of the nonwoven fabric simple body or the multilayer nonwoven fabric occurring in a case in which the nonwoven fabric simple body or the multilayer nonwoven fabric passed through the embossing rolls.

A: a state where the adhesion is not visually confirmed at all by visual observation.

B: a state where the adhesion is hardly confirmed by visual observation.

C: a state where the adhesion is confirmed by visual observation, or a wound state around the embossing rolls.

(3) Maximum Load Elongation [%]

Five test pieces of 50 mm (MD)×200 mm (CD) were sampled from the nonwoven fabric simple body or the multilayer nonwoven fabric. The test pieces were subjected to a tensile test using a constant speed extending type tensile tester under conditions of a chuck distance of 100 mm and a tensile speed of 100 mm/min, and the extension percentage of the test piece at the time when the load applied to the test piece became the maximum was measured. The average value of the five test pieces was determined and taken as maximum load elongation.

(4) Residual Strain [%]

Five test pieces of 250 mm (MD)×50 mm (CD) were cut out from the nonwoven fabric simple body or the multilayer nonwoven fabric. This test piece was drawn under conditions of a chuck distance of 30 mm, a tensile speed of 30 mm/min, and a draw ratio of 100%. Thereafter, the test piece was immediately recovered to the original length at the same speed, to obtain a stretchable nonwoven fabric. At that time, the strain was measured at the time when the tensile load reached 0 gf. The average value of the five nonwoven fabrics was evaluated as residual strain (unit: %).

(5) Stress at 50% Extending, Stress at 50% Recovering, Stretch Characteristics

Five test pieces of 25 mm (MD)×200 mm (CD) were sampled from the nonwoven fabric single body or the multilayer nonwoven fabric using a universal tensile tester (IM-201 type, manufactured by Intesco Co., Ltd.). Subsequently, each of the sampled test pieces was extended by 100% under conditions of a sample width of 25 mm, a chuck distance of 100 mm, and a tensile speed of 300 mm/min, and then immediately recovered to the original length at the same speed. One cycle of this operation was further repeated, and stress in a case in which a draw ratio became 50% during extending in the second cycle was defined as stress at 50% extending. Stress in a case in which a draw ratio became 50% during recovering in the second cycle was defined as stress at 50% recovering. Subsequently, the value of [stress at 50% extending+stress at 50% recovering] was measured as the measure of the stretch characteristics, and the average value of the five test pieces was evaluated as stretch characteristics. The smaller the value of [stress at 50% extending+stress at recovering at 50%] is, the more excellent the stretch characteristics are.

(6) Stickiness

Ten evaluators touched the nonwoven fabric simple body or the multilayer nonwoven fabric with their hands and evaluated the stickiness by the following criteria.

AA: all the 10 evaluators felt no stickiness and fine touch.

A: 9 to 7 evaluators of 10 evaluators felt no stickiness and fine touch.

B: 6 to 3 evaluators of 10 evaluators felt no stickiness and fine touch.

C: 2 to 0 evaluators of 10 evaluators felt no stickiness and fine touch.

(7) Low Temperature Heat Sealability

A multilayer nonwoven fabric and a nonwoven fabric peeled off from a commercially available disposable diaper were stacked one by one, and a heat-sealed sample was produced using a heat sealer under conditions of a temperature of 90° C., a pressure of 0.3 MPa, and a time of 1 second. Three test pieces of 250 mm (MD)×50 mm (CD) were sampled from the prepared sample. Subsequently, a packing tape was attached to each of both surfaces of a part of the test piece (20 mm from an end in the MD direction). Thereafter, the packing tape was manually pulled in both directions of the test piece, thereby peeling a layer of the multilayer nonwoven fabric by 100 mm. Thereafter, each peeled layer was set in a constant speed extending type tensile tester. A tensile test was conducted under conditions of a chuck distance of 100 mm and a tensile speed of 100 mm/min. The stress of the test piece at the time when a load applied to the test piece reached the maximum was measured. The average value of the three test pieces was evaluated as low temperature heat sealability. A case in which the test piece was firmly fixed such that the test piece was broken was defined as "material breaking".

Example 1

<Preparation of Thermoplastic Polyurethane Elastomer (TPU)>

71.7 parts by mass of a polyester polyol having a number average molecular weight of 1932, 4.8 parts by mass of 1,4-butanediol (hereinafter abbreviated as "BD"), 0.3 parts by mass of pentaerythritol tetrakis[3-(3,5-di-t-butyl-4-hydroxyphenyl)propionate (hereinafter abbreviated as "antioxidant-1"), and 0.3 parts by mass of polycarbodiimide were mixed to obtain a mixture, and 22.9 parts by mass of MDI was added to the mixture, followed by sufficiently performing high speed stirring and mixing. Thereafter, the reaction was carried out at 160° C. for 1 hour to obtain a reaction product. After the reaction product was pulverized, 0.8 parts by mass of ethylenebisstearic acid amide, 0.5 parts by mass of triethylene glycol-bis-[3-(3,5-di-t-butyl-4v hydroxyphenyl)propionate] (hereinafter abbreviated as "antioxidant-2"), and 0.8 part by mass of ethylene bisoleic acid amide (hereinafter abbreviated as "EOA") were mixed with 100 parts by mass of the pulverized product to obtain a mixture. Thereafter, the mixture was melt-kneaded in an extruder (set temperature: 210° C.) and granulated to obtain a thermoplastic polyurethane elastomer [TPU (A-1)].

The physical properties of the obtained TPU (A-1) were hardness: 81, melt viscosity: 1.1, and flow starting temperature: 155° C.

<Preparation of Thermoplastic Resin Composition for Mixed Fiber Spunbonded Nonwoven Fabric>

92 parts by mass of a propylene homopolymer (hereinafter abbreviated as "PP-1") having a MFR (measured at 230° C. under a load of 2.16 kg in accordance with ASTM D 1238) of 60 g/10 min, a density 0.91 g/cm$^3$, and a melting point of 160° C., and 8 parts by mass of a high density polyethylene (hereinafter abbreviated as "HDPE") having MFR (measured at 190° C. under a load of 2.16 kg in accordance with ASTM D 1238) of 5 g/10 min, a density of 0.97 g/cm$^3$ and a melting point of 134° C. were mixed to prepare a thermoplastic resin composition (B-1).

<Preparation of Low Crystalline Polypropylene for Elastic Nonwoven Fabric>

To a stainless steel reactor having an inner volume of 0.2 m$^3$ equipped with a stirrer, n-heptane at 20 L/h, triisobutylaluminum at 15 mmol/h, and a catalyst component obtained by preliminarily contacting dimethylanilinium tetrakispentafluorophenylborate, (1,2'-dimethylsilylene)(2,1'-dimethylsilylene)-bis(3-trimethylsilylmethylindenyl)zirconium dichloride, triisobutylaluminum, and propylene at 6 μmol/h per zirconium were continuously supplied.

Propylene and hydrogen were continuously supplied in a state where a hydrogen concentration in a gas phase portion was 8 mol % at a polymerization temperature of 70° C. and the total pressure in the reactor was maintained at 0.7 MPa·G To the obtained polymerization solution, 1000 ppm of SUMILIZER GP (manufactured by Sumitomo Chemical Co., Ltd.) was added, and the solvent was removed to obtain a low crystalline propylene polymer.

The low crystalline propylene polymer thus obtained had a weight-average molecular weight (Mw) of $1.2 \times 10^4$ and Mw/Mn of 2. According to NMR measurement, [mmmm] was 46 mol %; [rrrr]/(1−[mmmm]) was 0.038; [rmrm] was 2.7 mol %; and [mm]×[rr]/[mr]$^2$ was 1.5.

<Production of Multilayer Nonwoven Fabric>

Each of TPU (A-1) and the thermoplastic resin composition (B-1) prepared above was independently melted using an extruder having a diameter of 75 mm and an extruder having a diameter of 50 mm. Thereafter, these melted products were melt spun according to a spunbonding method using a spunbonded nonwoven fabric molding machine having a spinneret (length in a direction perpendicular to a machine direction on a collection surface: 800 mm) in such conditions that both a resin temperature and a die temperature were 205° C.; a cooling air temperature was 20° C.; and a drawing air velocity was 3200 m/min to deposit a web composed of mixed long fibers containing long fibers A composed of TPU (A-1) and long fibers B composed of the thermoplastic resin composition (B-1) on the collection surface.

Specifically, a nozzle pattern in which discharge holes for TPU (A-1) and discharge holes for the thermoplastic resin composition (B-1) were alternately arranged was used as the spinneret. The nozzle diameter for TPU (A-1) (long fiber A) was 0.75 mm, and the nozzle diameter for the thermoplastic resin composition (B-1) (long fiber B) was 0.6 mm. A nozzle pitch in a longitudinal direction was 8 mm, and a nozzle pitch in a lateral direction was 11 mm. The ratio of the number of nozzles for the long fibers A to the number of nozzles for the long fibers B was 1:1.45. The discharge amount of one hole for the long fibers A was 0.78 g/(minute·hole), and the discharge amount of one hole for the long fibers B was 0.59 g/(minute·hole). A spunbonded nonwoven fabric composed of the mixed long fibers was deposited as a first layer on the collection surface.

Subsequently, an elastic nonwoven fabric was deposited as a second layer on the mixed fiber spunbonded nonwoven fabric. Specifically, the low crystalline polypropylene produced by the above method was melted using a single screw extruder having a screw diameter of 75 mm. Thereafter, the melted product was melt spun according to a spunbonding method using a spunbonded nonwoven fabric molding machine having a spinneret (die, number of holes: 808) (length in the direction perpendicular to the machine direction on the collection surface: 800 mm) under conditions where both a resin temperature and a die temperature were 215° C.; a cooling air temperature was 20° C.; and a drawing air-blowing speed was 3750 m/min. Thus, a second layer was deposited.

Subsequently, the same mixed fiber spunbonded nonwoven fabric as the first layer was deposited as a third layer on the elastic nonwoven fabric by the same method as that of the first layer to prepare a three-layer deposit. This deposit was subjected to a thermal pressure treatment using embossing rolls (emboss area ratio: 18%, emboss temperature: 70° C.) to give a multilayer nonwoven fabric which had a total basis weight of 60.0 g/m², the basis weight of each of the first layer and the third layer being 20.0 g/m², the basis weight of the second layer being 20.0 g/m².

The multilayer nonwoven fabric obtained as described above hardly adhered to the surface of a metal roll in an embossing step, and exhibited good moldability. The physical properties of the obtained multilayer nonwoven fabric were measured, and the results are shown in Table 1.

Example 2

In the same manner as in Example 1, a web composed of mixed long fibers containing long fibers A composed of TPU (A-1) and long fibers B composed of a thermoplastic resin composition (B-1) was deposited as a first layer on a collection surface.

Subsequently, as a second layer, each of TPU (A-1) and the low crystalline polypropylene prepared in the same manner as in Example 1 was independently melted using an extruder having a diameter of 75 mm and an extruder having a diameter of 50 mm. Thereafter, these melted products were melt spun according to a spunbonding method using a spunbonded nonwoven fabric molding machine having a spinneret (length in a direction perpendicular to a machine direction on a collection surface: 800 mm) in such conditions that both a resin temperature and a die temperature were 205° C.; a cooling air temperature was 20° C.; and a drawing air velocity was 3200 m/min to deposit a web (elastic nonwoven fabric) composed of mixed long fibers containing 40% by mass of long fibers composed of TPU (A-1) and 60% by mass of long fibers composed of the low crystalline polypropylene on the web composed of the mixed long fibers of the first layer.

An elastic nonwoven fabric of a second layer was deposited on the web composed of the mixed long fibers of the first layer as follows. Specifically, a nozzle pattern in which discharge holes for TPU (A-1) and discharge holes for the low crystalline polypropylene were alternately arranged was used as the spinneret. The nozzle diameter for TPU (A-1) was 0.75 mm, and the nozzle diameter for the low crystalline polypropylene was 0.6 mm. A nozzle pitch in a longitudinal direction was 8 mm, and a nozzle pitch in a lateral direction was 11 mm. The ratio of the number of nozzles for long fibers A composed of TPU (A-1) to the number of nozzles for the low crystalline polypropylene was 1:1.45. The discharge amount of one hole for the long fibers composed of TPU (A-1) was 0.60 g/(minute-hole), and the discharge amount of one hole for the long fibers composed of the low crystalline polypropylene was 0.60 g/(minute-hole).

Subsequently, as a third layer, the same web composed of the mixed long fibers containing the long fibers A composed of TPU (A-1) and the long fibers B composed of a thermoplastic resin composition (B-1) as that of the first layer was deposited on the elastic nonwoven fabric of the second layer in the same manner as in the first layer to obtain a three-layer deposit. This deposit was subjected to a thermal pressure treatment using embossing rolls (emboss area ratio: 18%, emboss temperature: 90° C.) to give a multilayer nonwoven fabric which had a total basis weight of 60.0 g/m², the basis weight of each of the first layer and the third layer being 20.0 g/m², the basis weight of the second layer being 20.0 g/m².

The multilayer nonwoven fabric obtained as described above hardly adhered to the surface of a metal roll in an embossing step, and exhibited good moldability. The physical properties of the obtained multilayer nonwoven fabric were measured, and the results are shown in Table 1.

Comparative Example 1

TPU (A-1) produced by the method of Example 1 was melted using a single screw extruder having a screw diameter of 75 mm. Thereafter, the melted product was melt spun according to a spunbonding method using a spunbonded nonwoven fabric molding machine having a spinneret (length in a direction perpendicular to a machine direction on a collection surface: 800 mm) under conditions where both a resin temperature and a die temperature were 205° C.; a cooling air temperature was 20° C.; and a drawing air-blowing speed was 3200 m/min. Thus, long fibers A composed of TPU (A-1) were deposited on the collection surface. In a case in which this deposit was subjected to a thermal pressure treatment using embossing rolls (emboss area ratio: 18%, emboss temperature: 107° C.), the deposit adhered to the embossing rolls, which made it impossible to produce a desired TPU simple body nonwoven fabric.

Comparative Example 2

The low crystalline polypropylene produced in Example 1 was melted using a single screw extruder having a screw diameter of 75 mm. Thereafter, the melted product was melt spun according to a spunbonding method using a spunbonded nonwoven fabric molding machine having a spinneret (die, number of holes: 808) (length in a direction perpendicular to a machine direction on a collection surface: 800 mm) under conditions where both a resin temperature and a die temperature were 215° C.; a cooling air temperature was 20° C.; and a drawing air-blowing speed was 3750 m/min. Thus, a low crystalline polypropylene simple body nonwoven fabric was deposited on the collection surface. In a case in which this deposit was subjected to a thermal pressure treatment using embossing rolls (emboss area ratio: 18%, emboss temperature: 70° C.), the deposit adhered to the embossing rolls, which made it impossible to produce a desired low crystalline polypropylene simple body nonwoven fabric.

Comparative Example 3

A propylene homopolymer (hereinafter referred to as "polymer IA") having MFR (measured at 230° C. under a load of 2.16 kg in accordance with ASTM D 1238) of 8.5 g/10 min, a density 0.91 g/cm³, and a melting point of 160° C. was melted using an extruder having a diameter of 50 mm. A propylene homopolymer (hereinafter referred to as "polymer II") having MFR (measured in accordance with ASTM D 1238 at 230° C. under a load of 2.16 kg) of 60 g/10 min, a density of 0.91 g/cm³, and a melting point of 160° C. was independently melted using an extruder having a diameter of 75 mm. Thereafter, composite melt spinning was performed according to a spunbonding method using a spunbonded nonwoven fabric molding machine having a spinneret (die, number of holes: 2887) capable of molding a concentric sheath-core composite fiber in which the "polymer I" was a core and the "polymer II" was a sheath (length in a direction perpendicular to a machine direction on a collection surface: 800 mm) in such conditions that both a resin temperature and a die temperature were 250° C.; a cooling air temperature was 20° C.; and a drawing air velocity was 3750 m/min to deposit a spunbonded nonwoven fabric (sheath-core spunbonded nonwoven fabric) composed of the concentric sheath-core composite fiber having a core portion and a sheath portion at a mass ratio of 10/90 on the collection surface. This deposit was subjected to a thermal pressure treatment using embossing rolls (emboss area ratio: 18%, emboss temperature: 107° C.) to prepare a sheath-core spunbonded nonwoven fabric single body which had a total basis weight of 60.0 g/m².

The sheath-core spunbonded nonwoven fabric obtained as described above hardly adhered to the surface of a metal roll in an embossing step, and exhibited good moldability. The physical properties of the obtained sheath-core spunbonded nonwoven fabric were measured, and the results are shown in Table 1.

Comparative Example 4

Each of TPU (A-1) and the thermoplastic resin composition (B-1) prepared in Example 1 was independently melted using an extruder having a diameter of 75 mm and an extruder having a diameter of 50 mm. Thereafter, these melted products were melt spun according to a spunbonding method using a spunbonded nonwoven fabric molding machine having a spinneret (length in a direction perpendicular to a machine direction on a collection surface: 800 mm) in such conditions that both a resin temperature and a die temperature were 205° C.; a cooling air temperature was 20° C.; and a drawing air velocity was 3200 m/min to deposit a web composed of mixed long fibers containing long fibers A composed of TPU (A-1) and long fibers B composed of the thermoplastic resin composition (B-1) on the collection surface.

Specifically, a nozzle pattern in which discharge holes for TPU (A-1) and discharge holes for the thermoplastic resin composition (B-1) were alternately arranged was used as the spinneret. The nozzle diameter for TPU (A-1) (long fiber A) was 0.75 mm, and the nozzle diameter for the thermoplastic resin composition (B-1) (long fiber B) was 0.6 mm. A nozzle pitch in a longitudinal direction was 8 mm, and a nozzle pitch in a lateral direction was 11 mm. The ratio of the number of nozzles for the long fibers A to the number of nozzles for the long fibers B was 1:1.45. The discharge amount of one hole for the long fibers A was 0.78 g/(minute-hole), and the discharge amount of one hole for the long fibers B was 0.59 g/(minute-hole). A deposit composed of the mixed long fibers was deposited on the collection surface. This deposit was subjected to a thermal pressure treatment using embossing rolls (emboss area ratio: 18%, emboss temperature: 107° C.) to prepare a mixed fiber spunbonded nonwoven fabric which had a total basis weight of 60.0 g/m².

The mixed fiber spunbonded nonwoven fabric obtained as described above hardly adhered to the surface of a metal roll in an embossing step, and exhibited good moldability.

The physical properties of the obtained mixed fiber spunbonded nonwoven fabric were measured, and the results are shown in Table 1.

Comparative Example 5

A sheath-core spunbonded nonwoven fabric was deposited as a first layer on a collection surface in the same manner as in Comparative Example 3 except that a basis weight was 20.0 g/m².

Subsequently, the low crystalline polypropylene produced by the method of Example 1 was melted using a single screw extruder having a screw diameter of 75 mm, and then melt spun according to a spunbonding method using a spunbonded nonwoven fabric molding machine having a spinneret (die, number of holes: 808) (length in a direction perpendicular to a machine direction on a collection surface: 800 mm) under conditions where both a resin temperature and a die temperature were 215° C.; a cooling air temperature was 20° C.; and a drawing air-blowing speed was 3750 m/min. Thus, an elastic nonwoven fabric having a basis weight of 20.0 g/m² was deposited on the sheath-core spunbonded nonwoven fabric of the first layer.

Subsequently, the same sheath-core spunbonded nonwoven fabric as the first layer was deposited as a third layer on the elastic nonwoven fabric of the second layer by the same method as that of the first layer to prepare a three-layer deposit. This deposit was subjected to a thermal pressure treatment using embossing rolls (emboss area ratio: 18%, emboss temperature: 70° C.) to give a multilayer nonwoven fabric which had a total basis weight of 60.0 g/m², the basis weight of each of the sheath-core spunbonded nonwoven fabrics of the first layer and the third layer being 20.0 g/m², the basis weight of the elastic nonwoven fabric of the second layer being 20.0 g/m².

The multilayer nonwoven fabric obtained as described above hardly adhered to the surface of a metal roll in an embossing step, and exhibited good moldability. The physical properties of the obtained multilayer nonwoven fabric were measured, and the results are shown in Table 1.

As can be seen from comparison with Comparative Example 5, Example 1 had unchanged stress at 50% extending and only increased stress at 50% recovering. As a result, Example 1 had low stretch characteristics (stress at 50% extending/stress at 50% recovering) to provide improved stretchability.

TABLE 1

| Form | Item | | Example 1 | | Example 2 | | Comparative Example 1 | |
|---|---|---|---|---|---|---|---|---|
| Spunbonded nonwoven fabric (a) | Fiber shape | — | Multilayer Mixed fiber | | Multilayer Mixed fiber | | Simple body Single fiber | |
| | Resin | — | Thermoplastic elastomer (A) | Thermoplastic resin (B) | Thermoplastic elastomer (A) | Thermoplastic resin (B) | Thermoplastic elastomer (A) | Thermoplastic resin (B) |
| | | | TPU | hPP-1/HDPE | TPU | hPP-1/HDPE | TPU | — |
| | Ratio | [% by mass] | 47 | 53 | 47 | 53 | 100 | — |
| | Basis weight | [g/m²] | 20.0 | | 20.0 | | 60.0 | |
| | Spinnability | — | Very good | | Very good | | Very good | |
| Elastic nonwoven fabric (b) | Fiber shape | — | Simple fiber | | Mixed fiber | | — | |
| | Resin | — | Low crystalline PP | | Low crystalline PP | TPU | — | |
| | Ratio | [% by mass] | 100 | | 60 | 40 | — | |
| | Basis weight | [g/m²] | 20.0 | | 20.0 | | — | |
| | Spinnability | — | Very good | | Very good | | — | |
| Multilayer nonwoven fabric (a/b/a) | Total basis weight | [g/m²] | 60.0 | | 60.0 | | 60.0 | |
| | Moldability | [—] | A | | A | | C | |
| | Maximum load elongation | [%] | 211 | | 245 | | Impossible evaluation | |
| | Residual strain | [%] | 17.4 | | 16.3 | | Impossible evaluation | |
| | Stress at 50% extending | [N/50 mm] | 1.0 | | 0.8 | | Impossible evaluation | |
| | Stress at 50% recovering | [N/50 mm] | 0.40 | | 0.30 | | Impossible evaluation | |
| | Stretch characteristics | [—] | 2.5 | | 2.7 | | Impossible evaluation | |
| | Stickiness | [—] | A | | A | | Impossible evaluation | |
| | Low temperature heat sealability | [N/50 mm] | >18.5 (material breaking) | | 12.4 | | Impossible evaluation | |

| Form | Item | | Comparative Example 2 | | Comparative Example 3 | |
|---|---|---|---|---|---|---|
| Spunbonded nonwoven fabric (a) | Fiber shape | — | Simple body | | Simple body Sheath-core fiber | |
| | Resin | — | Thermoplastic elastomer (A) | Thermoplastic resin (B) | Thermoplastic elastomer (A) | Thermoplastic resin (B) |
| | | | — | — | — | hPP-1/hPP-2 |
| | Ratio | [% by mass] | — | — | — | 100 |
| | Basis weight | [g/m²] | — | | 60.0 | |
| | Spinnability | — | — | | Very good | |
| Elastic nonwoven fabric (b) | Fiber shape | — | Simple fiber | | — | |
| | Resin | — | Low crystalline PP | | — | |
| | Ratio | [% by mass] | 100 | | — | |
| | Basis weight | [g/m²] | 60.0 | | — | |
| | Spinnability | — | Very good | | — | |
| Multilayer nonwoven fabric (a/b/a) | Total basis weight | [g/m²] | 60.0 | | 60.0 | |
| | Moldability | [—] | C | | A | |
| | Maximum load elongation | [%] | Impossible evaluation | | 201 | |
| | Residual strain | [%] | Impossible evaluation | | 64.8 | |
| | Stress at 50% extending | [N/50 mm] | Impossible evaluation | | 0.0 | |
| | Stress at 50% recovering | [N/50 mm] | Impossible evaluation | | 0.0 | |
| | Stretch characteristics | [—] | Impossible evaluation | | — | |
| | Stickiness | [—] | Impossible evaluation | | A | |
| | Low temperature heat sealability | [N/50 mm] | Impossible evaluation | | <0.1 | |

TABLE 1-continued

|  |  |  | Comparative Example 4 | | Comparative Example 5 | |
|---|---|---|---|---|---|---|
| Form Spunbonded nonwoven fabric (a) | Item | — | Simple body | | Multilayer | |
| | Fiber shape | — | Mixed fiber | | Sheath-core fiber | |
| | Resin | — | Thermoplastic elastomer (A) | Thermoplastic resin (B) | Thermoplastic elastomer (A) | Thermoplastic resin (B) |
| | | | TPU | hPP-1/HDPE | — | hPP-1/hPP-2 |
| | Ratio | [% by mass] | 47 | 53 | — | 100 |
| | weight | [g/m²] | 60.0 | | 20.0 | |
| | Spinnability | — | Very good | | Very good | |
| Elastic nonwoven fabric (b) | Fiber shape | — | — | | Simple fiber | |
| | Resin | — | — | | Low crystalline PP | |
| | Ratio | [% by mass] | — | | 100 | |
| | Basis weight | [g/m²] | — | | 20.0 | |
| | Spinnability | — | — | | Very good | |
| Multilayer nonwoven fabric (a/b/a) | Total basis weight | [g/m²] | 60.0 | | 60.0 | |
| | Moldability | [—] | A | | A | |
| | Maximum load elongation | [%] | 293 | | 205 | |
| | Residual strain | [%] | 22.3 | | 21.7 | |
| | Stress at 50% extending | [N/50 mm] | 0.55 | | 1.0 | |
| | Stress at 50% recovering | [N/50 mm] | 0.17 | | 0.25 | |
| | Stretch characteristics | [—] | 3.2 | | 4.0 | |
| | Stickiness | [—] | A | | A | |
| | Low temperature heat sealability | [N/50 mm] | 1.6 | | 9.1 | |

The disclosure of Japanese Patent Application No. 2015-046378 is hereby incorporated by reference in its entirety. All the publications, patent applications, and technical standards described in the present specification are incorporated by reference to the same extent as if each individual publication, patent application, and technical standard are specifically and individually described to be incorporated by reference.

The invention claimed is:

1. A multilayer nonwoven fabric, comprising:
an elastic nonwoven fabric containing a long fiber of a first thermoplastic elastomer (A') and a low crystalline polypropylene satisfying the following (a) to (f); and
two mixed fiber spunbonded nonwoven fabrics,
wherein the multilayer nonwoven fabric has a three-layer structure including the mixed fiber spunbonded nonwoven fabric, the elastic nonwoven fabric and the mixed fiber spunbonded nonwoven fabric, in this order,
wherein each of the mixed fiber spunbonded nonwoven fabrics contains a long fiber of a second thermoplastic elastomer (A) and a long fiber of a thermoplastic resin (B) other than the second thermoplastic elastomer (A) in a ratio of 10 to 90% by mass:90 to 10% by mass ((A):(B), with the proviso that (A)+(B)=100% by mass), and
wherein the thermoplastic resin (B) is an olefinic polymer composition consisting essentially of a propylene polymer and a high-density polyethylene:
(a) [mmmm]=20 to 60 mol %;
(b) [rrrr]/(1−[mmmm])<0.1;
(c) [rmrm]>2.5 mol %;
(d) [mm]×[rr]/[(mr)]²<2.0;
(e) weight-average molecular weight (Mw)=10,000 to 200,000; and
(f) molecular weight distribution (Mw/Mn)<4,
wherein:
[mmmm] is a mesopentad fraction;
[rrrr] is a racemic pentad fraction;
[rmrm] is a racemic meso racemic mesopentad fraction; and
[mm], [rr] and [mr] are triad fractions,
wherein the first thermoplastic elastomer (A') includes a first thermoplastic polyurethane elastomer, and the second thermoplastic elastomer (A) includes a second thermoplastic polyurethane elastomer,
wherein a mixing ratio of the first thermoplastic polyurethane elastomer in the elastic nonwoven fabric is greater than 0% and up to 40% by mass, and is smaller than a mixing ratio of the second thermoplastic polyurethane elastomer in any one of the two mixed fiber spunbonded nonwoven fabrics, and
wherein low temperature heat sealability of the multilayer nonwoven fabric is from 10 N/50 mm to about 18.5 N/50 mm.

2. The multilayer nonwoven fabric according to claim 1, wherein a maximum point elongation of the long fiber of the thermoplastic resin (B), in a case of being formed into the spunbonded nonwoven fabric, is 50% or more.

3. The multilayer nonwoven fabric according to claim 1, wherein the first thermoplastic elastomer (A') is the first thermoplastic polyurethane elastomer, and the second thermoplastic elastomer (A) is the second thermoplastic polyurethane elastomer.

4. The multilayer nonwoven fabric according to claim 1, wherein:
the first or second thermoplastic polyurethane elastomer has a solidification starting temperature of 65° C. or higher as measured by a differential scanning calorimeter (DSC); and a number of particles of the first or second thermoplastic polyurethane elastomer insoluble in a dimethylacetamide solvent measured by a particle size distribution measuring apparatus equipped with an aperture of 100 μm based on a pore electrical resistance method, is 3,000,000/g or less.

5. The multilayer nonwoven fabric according to claim 1, wherein the first or second thermoplastic polyurethane elastomer is a thermoplastic polyurethane elastomer satisfying the following relational expression (I):

$$a/(a+b) \leq 0.8 \tag{I}$$

wherein:
a represents a total amount of fusion heat calculated from an endothermic peak in a range of 90° C. to 140° C., as measured by DSC; and
b represents a total amount of fusion heat calculated from an endothermic peak in a range from higher than 140° C. to 220° C. or lower, as measured by DSC.

6. The multilayer nonwoven fabric according to claim 1, wherein the thermoplastic resin (B) consists essentially of 99 to 80% by mass of the propylene polymer and 1 to 20% by mass of the high-density polyethylene.

7. A stretchable multilayer nonwoven fabric obtained by drawing the multilayer nonwoven fabric according to claim 1.

8. A fiber product comprising the multilayer nonwoven fabric according to claim 1.

9. An absorbent article comprising the multilayer nonwoven fabric according to claim 1.

10. A sanitary mask comprising the multilayer nonwoven fabric according to claim 1.

11. A fiber product comprising the stretchable multilayer nonwoven fabric according to claim 6.

12. An absorbent article comprising the stretchable multilayer nonwoven fabric according to claim 6.

13. A sanitary mask comprising the stretchable multilayer nonwoven fabric according to claim 6.

* * * * *